United States Patent [19]

Case

[11] 3,983,867
[45] Oct. 5, 1976

[54] METHOD AND APPARATUS FOR PROVIDING HEXAXIAL ECG DISPLAY

[76] Inventor: Robert Case, 130 E. 75th St., New York, N.Y. 10021

[22] Filed: Sept. 29, 1975

[21] Appl. No.: 617,981

[52] U.S. Cl. .......................... 128/2.06 G; 128/206 B
[51] Int. Cl.² ........................................... A61B 5/04
[58] Field of Search .................. 128/2.06 B, 2.06 G, 128/2.06 R, 2.06 V, 2.05 R

[56] References Cited
UNITED STATES PATENTS

| | | | |
|---|---|---|---|
| 2,098,695 | 11/1937 | Southwick | 128/2.06 B |
| 2,714,380 | 8/1955 | Freshman | 128/2.06 V |
| 3,058,458 | 10/1962 | Daneman | 128/2.06 B |
| 3,256,733 | 6/1966 | Carlin | 128/2.06 R |
| 3,585,988 | 6/1971 | Creigh et al. | 128/2.06 G |
| 3,707,147 | 12/1972 | Sellers | 128/2.06 G |
| 3,868,948 | 3/1975 | Graetz | 128/2.06 G |

*Primary Examiner*—William E. Kamm
*Attorney, Agent, or Firm*—Hubbell, Cohen, Stiefel & Gross

[57] ABSTRACT

A 360° hexaxial reference system orthogonal display of voltage versus time generated in response to heart activity is directly provided with the display having 30° angular separation between adjacent electrode pair potential difference electrocardiographic sampled voltages. Both Einthoven bipolar leads and augmented V unipolar leads, each of which comprise an electrode pair, are disposed at predetermined locations with respect to the arms and legs of the body of a patient whose heart activity is to be diagnosed. Sequential selection of the electrode pairs one-by-one, from the plurality of bipolar and unipolar electrode pairs together with selective polarity reversal of the potential differences associated with the various leads for the electrode pairs is accomplished to provide the 30° angular separation between adjacent electrode pair potential differences for directly providing the 360° hexaxial reference system orthogonal display. The display which respectively comprises lead I, lead AVR with the polarity reversed, lead II, lead AVF, lead III, lead AVL with the polarity reversed, lead I with the polarity reversed, lead AVR, lead II with the polarity reversed, lead AVF with the polarity reversed, lead III with the polarity reversed, and lead AVL will respectively provide vectors at 0°, 30°, 60°, 90°, 120°, 150°, 180°, −150°, −120°, −90°, −60°, and −30°, whereby cardiogram analysis including determination of the mean vector is enhanced.

9 Claims, 18 Drawing Figures

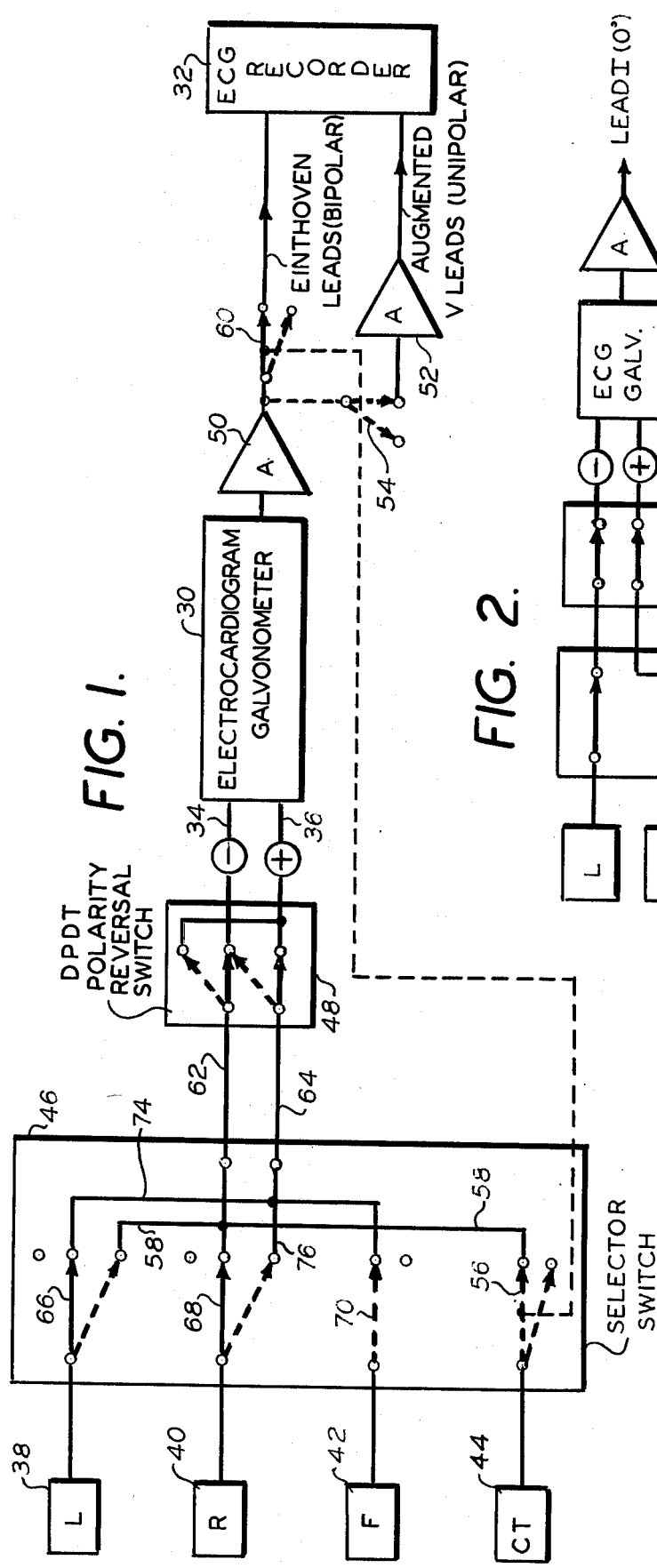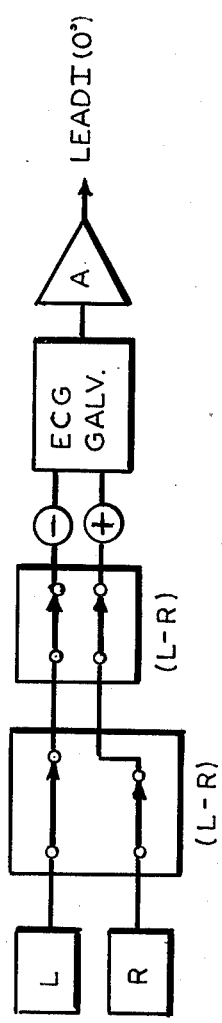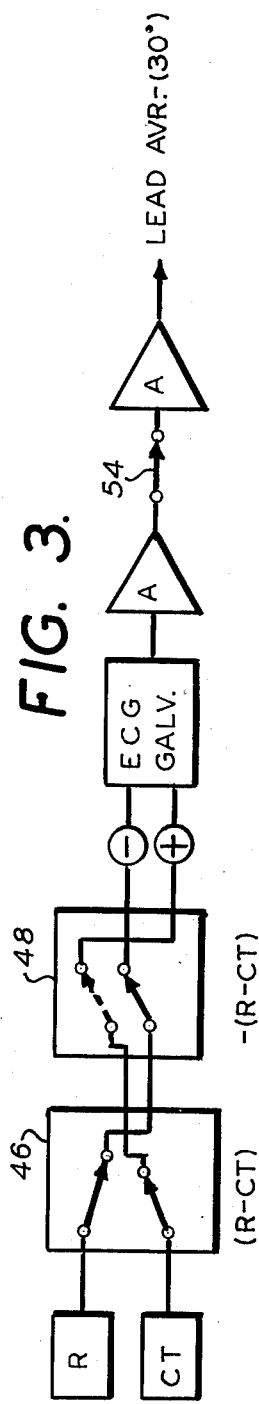
FIG. 1.
FIG. 2.
FIG. 3.

AVR

AVL

AVF

METHOD AND APPARATUS FOR PROVIDING HEXAXIAL ECG DISPLAY

BACKGROUND OF THE INVENTION

1. Field of the Invention

The present invention relates to methods and apparatus for use in electrocardiography.

2. Description of the Prior Art

Present day electrocardiography is performed primarily either by analysis of a spatial vector in which the voltage generated by the heart in one axis is observed in relation to the simultaneous voltage generated in the perpendicular axis, such procedure being known as vectorcardiography, or by analysis of the recorded voltage versus time generated at several points on the surface of the patient's body, such approach being conventionally known as electrocardiogram or ECG. The latter is a method in routine use clinically. The various sites in the body utilized for such electrocardiogram recording, the terminology, and the connections utilized have been standardized by the American Heart Association, such as enumerated in the Report of the Committee on Electrocardiography of the American Heart Association, Circulation 10: 564, 1954, entitled "Recommendations for Standardization of Electrocardiographic and Vectorcardiographic Leads", by Kossman, et al or in another such report, Circulation 35: 583, 1967 entitled "Recommendations for Standardization of Leads and Specifications for Instruments in Electrocardiography and Vectorcardiography", by Kossman et al, and all electrocardiographic machines in the United States rely on such recording techniques. In such conventional standardized systems, in the frontal plane, which is the plane parallel to the body, electrodes are placed on the left arm, generally represented by the letter L, the right arm generally represented by the letter R, and the left leg, generally represented by the letter F, and usually the right leg for a ground, these leads being known as the Einthoven leads which are bipolar leads. Lead I of the Einthoven leads represents the voltage or potential difference between the left arm and the right arm and is represented by the expression L—R; lead II of the Einthoven leads provides the voltage or potential difference between the left leg and the right arm and is represented by the expression F—R; and lead III of the Einthoven leads provides the voltage or potential difference between the left leg and the left arm and is represented by the expression F—L. In addition, in certain prior art electrocardiographic systems, unipolar augmented V leads, such as the type described by Goldberger in a text entitled "Unipolar Lead Electrocardiography", published in Philadelphia in 1949, Second Edition, are utilized as follows: lead AVL, which provides the voltage or potential difference between the left arm and a central terminal as illustrated in FIGS. 14 through 16, where the central terminal is represented by the symbol CT and this potential difference is represented by the expression L—CT; the lead AVR, which provides the voltage or potential difference between the right arm and the central terminal is represented by the expression R—CT; and the lead AVL, which provides the voltage or potential difference between the left leg and the central terminal and is represented by the expression F—CT. An electrocardiogram utilizing the bipolar aand unipolar leads is conventionally provided such as in a typical instrument utilizing a Beckman Type R Dynograph utilizing a No. 9855 Electrocardiogram Input Coupler. These various lead systems, which are conventional, are described in several cardiology textbooks, such as a text entitled "Electrocardiography and Vectorcardiography" by Lamb, published in Philadelphia in 1965, and another textbook entitled "Clinical and Vector Electrocardiography", by Massie and Walsh, published in Chicago, in 1960. In the frontal plane, the six conventionally utilized leads, I, II, III, AVF, AVR and AVL, theoretically fit into an angular relationship which is commonly termed the hexaxial reference system and which is in common usage as a basis for interpreting electrocardiograms and is thoroughly described in the afore-mentioned cardiology textbooks. The lead in which electrocardiogram or ECG changes occur is of great diagnostic value in interpreting the cardiac disease process present, the interpretation of electrocardiograms being dependent on the particular lead in which changes occur. The hexaxial reference system which has been developed has been of assistance in diagnosis and in understanding of the inter-relationships of the various lead systems. However, as presently recorded in conventional electrocardiograms, the angular equivalent of the leads are 0°, 60°, 120°, −150°, −30°, and 90° representing respectively leads I, II, III, AVR, AVL and AVF, which are displayed in that order. Any other angular representations must be imagined by utilizing mental gymnastics. These mental gymnastics are necessarily required in determining the mean vector which has become an important diagnostic determinant for many forms of heart disease, the diagnosis of a particular disease being dependent on the angle of the mean vector. This mean vector angle is normally determined most quickly by observing the lead at which the least forces are developed, each lead representing the electrical force generated by the heart as viewed from a particular selected and specified angle in relation to the site of force generation. The mean vector is recognized as being perpendicular to this lead. Thus, a certain amount of mental gymnastics for each interpretation is required because of the type of display conventionally provided by electrocardiograms. Efforts have been made to minimize the mental gymnastics involved, such as by utilizing complex electronic systems to provide the mean vector as an output of the system, such as described in U.S. Pat. No. 3,548,813 or, as an aid in determining this mean vector, spatial vectometers, such as described in U.S. Pat. No. 2,714,380 have been developed. However these prior art systems have not become widely accepted and mental gymnastics is still required in interpreting present day electrocardiograms. In addition, prior art conventional cardiograms are not satisfactorily readily interpretable for certain types of myocardial infarctions such as posterior myocardial infarctions.

SUMMARY OF THE INVENTION

A method and apparatus for directly providing a 360° hexaxial reference system orthogonal display having 30° angular separation between adjacent electrode pair potential difference electrocardiographic sampled voltages is provided, whereby cardiogram analysis including determination of the mean vector is enhanced. In an electrocardiographic diagnostic apparatus having a plurality of electrodes disposable at predetermined locations with respect to the arms and legs of the body of the patient whose heart activity is to be diagnosed to provide both Einthoven bipolar leads and augmented V unipolar leads, each of the leads comprising an electrode pair, the diagnostic apparatus including display means for providing an orthogonal electrocardiogram display of voltage versus time generated at the predetermined location in response to such heart activity, the improvement comprises means connectable to the electrodes for receiving output signals therefrom for sequentially selecting one of the electrode pairs from the plurality of bipolar and unipolar electrode pairs for providing the display as well as selectable polarity reversal means connected between the electrode pair selection means and the display means for selectively reversing the associated polarity of the voltage potential differences for directly providing the 360° hexaxial reference system orthogonal display. The bipolar leads are disposed so as to provide time sampled voltages comprising a first voltage potential difference having an associated polarity between the left arm and right arm electrode pair for the patient represented by the expression L—R, a second voltage potential difference having an associated polarity between the left leg and the right arm electrode pair for the patient represented by the expression F—R, and a third voltage potential difference having an associated polarity between the left leg and the left arm electrode pair for the patient represented by the expression F—L, where L represents the potential at the left arm electrode location, R represents the potential at the right arm electrode location and F represents the potential at the left leg electrode location. The unipolar electrode pairs are disposed with respect to a central electrode terminal so as to provide a fourth voltage potential difference having an associated polarity between the left arm electrode and the central electrode terminal represented by the expression L—CT, a fifth voltage potential difference having an associated polarity between the right arm electrode and the central electrode terminal represented by the expression R—CT, and a sixth voltage potential difference having an associated polarity between the left leg electrode and the central electrode terminal represented by the expression F—CT, where CT represents the potential at the central electrode terminal. The hexaxial reference system orthogonal display comprises a contiguous sequential display having 30° gradations over the entire 360° presented from 0° to +180° and from 0° to −180° utilizing the conventional leads I, II, III, AVR, AVL and AVF as well as their inversion or polarity reversal, so as to result in presentations at any 30° angle with lead I being at 0°, the inversion of lead AVR being at 30°, lead II being at 60°, lead AVF being at 90°, lead III being at 120°, the inversion of lead AVL being at 150°, the inversion of lead I being at 180°, lead AVR being at −150°, the inversion of lead II being at −120°, the inversion of lead AVF being at −90°, the inversion of lead III being at −60°, and lead AVL being at −30°. Preferably, the augmented leads AVR, AVL and AVF, are amplified by substantially 13% so as to provide exact correspondence between voltages on any given vector between the augmented V leads and leads I, II, and III since the augmented V leads normally result in a projected voltage on a given vector of substantially 87% of that projected according to leads I, II, or III.

BRIEF DESCRIPTION OF DRAWINGS

FIG. 1 is a diagramatic illustration, partially in block, of the improved electrocardiographic diagnostic apparatus of the present invention;

FIGS. 2 through 13 are diagramatic illustrations, partially in block, of various positions of the selector switch and the polarity reversal switch for the embodiment illustrated in FIG. 1 to provide the 30° gradations over the entire 360° of a hexaxial reference system utilizing the Einthoven and augmented V leads and their inversions;

DETAILED DESCRIPTION OF THE PREFERRED EMBODIMENTS

Figure 14:
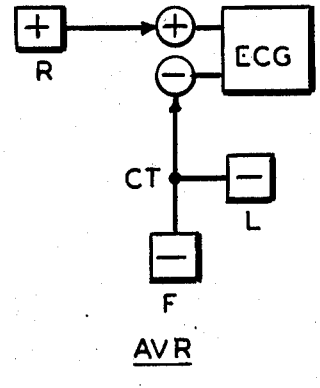
FIGS. 14 through 16 are diagramatic illustrations of the prior art augmented V leads according to Goldberger.
Figure 15:
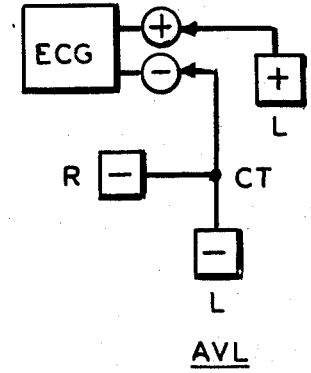
Figure 16:
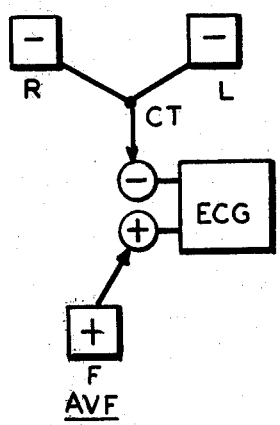

Referring now to FIG. 1, the present invention represents an improvement in conventional electrocardiographic diagnostic devices, such as typical conventional instruments utilizing a Beckman Type R Dynograph with a No. 9855 Electrocardiogram Input Coupler. For purposes of clarity, the bulk of the conventional circuitry associated with a conventional electrocardiograph device has been omitted with the conventional portion of the circuitry being represented by the block in FIG. 1 labeled "ELECTROCARDIOGRAM GALVANOMETER" and given reference numeral 30. The display device for the electrocardiogram is preferably a conventional electrocardiogram or ECG recorder generally represented by reference numeral 32. The negative and positive polarity leads to the galvanometer 30 are represented by paths 34 and 36 in FIG. 1. As will be described in greater detail hereinafter, the conventional electrodes normally utilized for providing an electrocardiogram are utilized in the present invention with these electrodes being respectively labeled L for the left arm, R for the right arm, and F for the left leg and being given reference numerals 38, 40, and 42 respectively and, in order to provide the augmented V leads, a common terminal represented by the letters CT given reference numeral 44, is also provided. The conventional connection of the respective left arm, right arm, left leg and common terminal electrodes to provide the augmented V leads, AVL, AVR, and AVF, which are conventional, is illustrated in FIGS. 14 through 16, with FIG. 14 representing the AVR lead, FIG. 15 representing the AVL lead, and FIG. 16 representing the AVF lead. These various electrodes 38 through 42 which are disposed at predetermined locations on the body of the patient whose heart activity is to be monitored or diagnosed, with these locations preferably being the conventional bipolar and unipolar locations to provide the conventional Einthoven leads, lead I, lead II, lead III, and the conventional augmented V leads, lead AVL, lead AVR, and lead AVF, such as described by Goldberger, are provided to a selector switch, generally represented by reference numeral 46, which enables selection of the appropriate electrode pair for sequentially providing time sampled voltages generated at the predetermined locations of the electrodes in response to heart activity. The output electrode pair of selector switch 46 is fed to a reversal switch 48 for inverting or reversing the polarity of the voltage or potential difference provided by the selected electrode pair so that, as will be described in greater detail hereinafter, a 360° hexaxial reference system orthogonal display of voltage versus time generated at the predetermined locations in response to the heart activity having 30° angular separation between adjacent electrode pair potential difference electrocardiographic sampled voltages may be provided.

The output of the polarity reversal switch 48, which is provided via paths 34 and 36, is provided to the galvanometer 30 whose output is in turn provided to a conventional amplifier 50 prior to being provided to the conventional recorder 32 for providing the electrocardiogram. As shown and preferred in FIG. 1, an additional amplifier 52, which is a conventional amplifier, is also preferably provided for the augmented V leads so as to preferably amplify the voltage output provided by the augmented V leads by substantially 13% in order to provide exact correspondence between the voltages on any given vector between the augmented V leads and leads I, II, and III since the augmented V leads normally resultant in a projected voltage on a given vector of substantially 87% of that projected according to leads I, II, or III. It should be noted that while this amplification is preferred, it is not necessary for the preferred angular electrocardiogram method because of the relatively small differences involved and may be omitted if desired. As shown and preferred in FIG. 1, amplifier 52 is connected to the output of amplifier 50 via a conventional switch 54 which is preferably ganged through the selector switch 56 associated with the common terminal 44 since when the common terminal is in the position shown connecting it to path 58, the output being provided will be from the augmented V leads so that ganged switch 54 will preferably be in a position to connect the input of amplifier 52 to the output of amplifier 50. At this time, another switch 60 which directly connects the output of amplifier 50 to the input of recorder 32 is open. Switch 60 is closed and switch 54 ganged thereto opened when the Einthoven lead inputs are being provided to the recorder 32. The input pair from the selector switch 46 to the polarity reversal switch 48 is provided via paths 62 and 64 with the selector switch associated with electrode 38 being represented by reference numeral 66, the selector switch associated with electrode 40 being represented by reference numeral 68 and the selector switch associated with electrode 42 being represented by reference numeral 70, the associated path, to switches 66, 68 and 70 being represented by path 74, the path, to switches 66, 68 and 56 being represented by previously mentioned reference numeral 58, and a single path between switch 68 and path 64 being represented by path 76.

Figure 17:
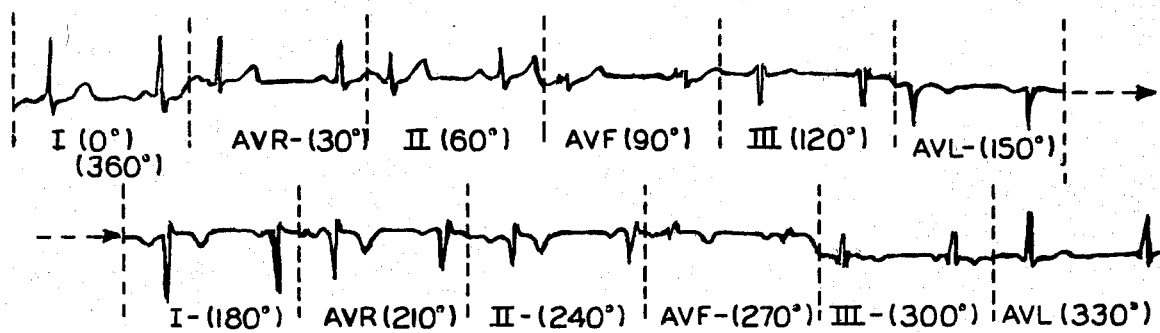
FIG. 17 is a diagramatic illustration of a typical hexaxial reference system orthogonal ECG longitudinal recording in accordance with the present invention.
Figure 18:
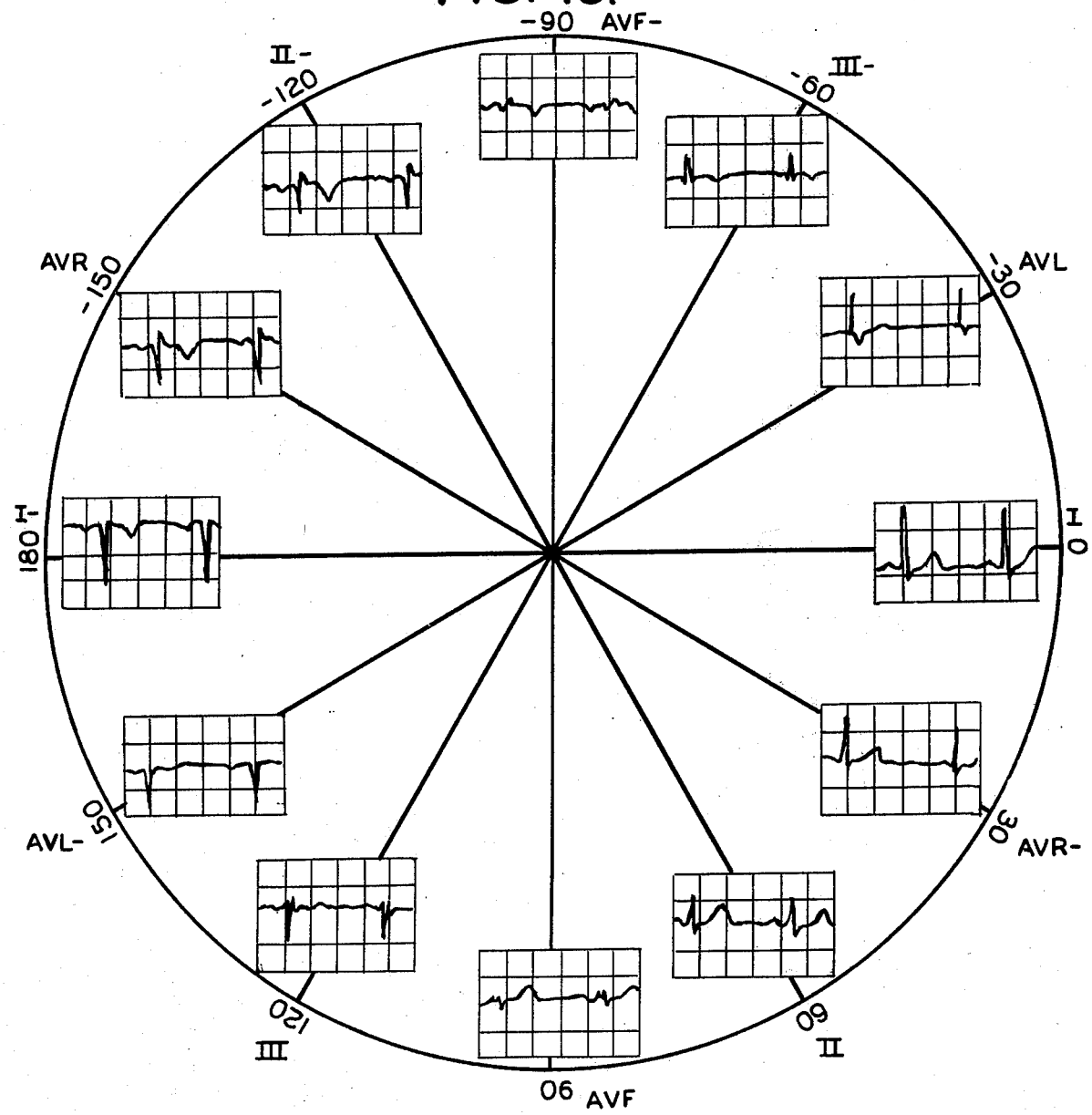
FIG. 18 is a diagramatic illustration of the hexaxial reference system illustrated in FIG. 17 arranged in a vectoral array.

Referring now to FIG. 18, a vectoral hexaxial reference system display illustrative of the type of display provided in accordance with the present invention is shown although the display in accordance with the present invention is preferably a more conventional orthogonal longitudinal type display as illustrated in FIG. 17 which corresponds to the display in FIG. 18. The conventional leads are represented by I, II, III, AVL, AVF and AVR in FIGS. 17 and 18, and the corresponding ones of FIGS. 2 through 16, and the inversion or reversed polarity corresponding to each of these leads is represented by the lead designation followed by a minus sign, such as the inversion of lead I being represented by I−, the inversion of lead II being represented by II−, the inversion of lead III being represented by III−, the inversion of lead AVR being represented by AVR−, the inversion of lead AVL being represented by AVL− and the inversion of lead AVF being represented by AVF−. As is shown and preferred in FIGS. 17 and 18, the angular vectoral location of lead I is at 0° in a 360° hexaxial reference system, the angular vectoral location of lead AVR− is at 30°, the angular vectoral location of lead II is at 60°, the angular vectoral location of lead AVF is at 90°, the angular vectoral location of lead III is at 120°, the angular vectoral location of lead AVL− is at 150°, the angular vectoral location of lead I− is at 180°, the angular vectoral location of lead AVR is at −150° (210°), the angular vectoral location of lead II− is at −120° (240°), the angular vectoral location of lead AVF− is at −90° (270°), the angular vectoral location of lead III− is at −60° (300°), and the angular vectoral location of lead AVL is at −30° (330°), which provides a complete 360° hexaxial reference system with leads I−, II−, III−, AVL−, AVF− and AVR− providing additional information which was not previously provided in conventional electrocardiographic systems. Thus, if it is desired to rapidly locate the mean vector, the user merely has to look at the electrocardiogram such as represented by FIG. 17 and select the least active lead, whether it be lead I, lead II, lead III, lead AVL, lead AVR, lead AVF or the inversions thereof represented by leads I−, II−, III−, AVL−, AVR− and AVF−, then, thereafter, add (or subtract) 90° to determine the angular location of the mean vector. Thus, in the example illustrated in FIG. 17, the least active lead appears to be lead II and, accordingly, the mean vector would have an angular location of −30° in the hexaxial reference system.

Figure 4:
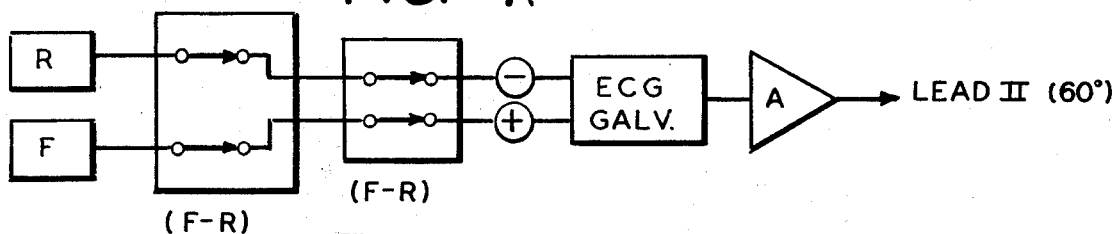
Figure 5:
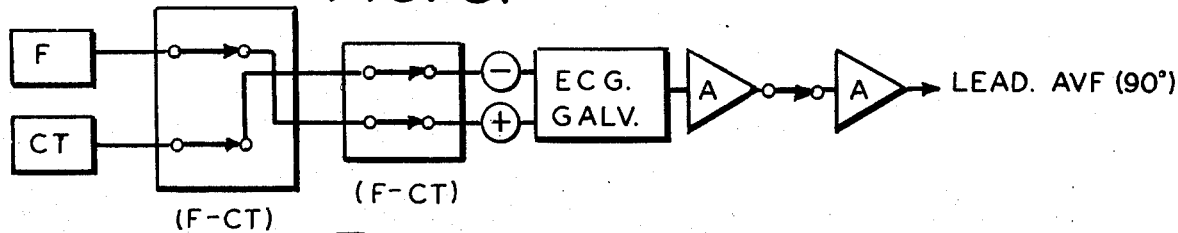
Figure 6:
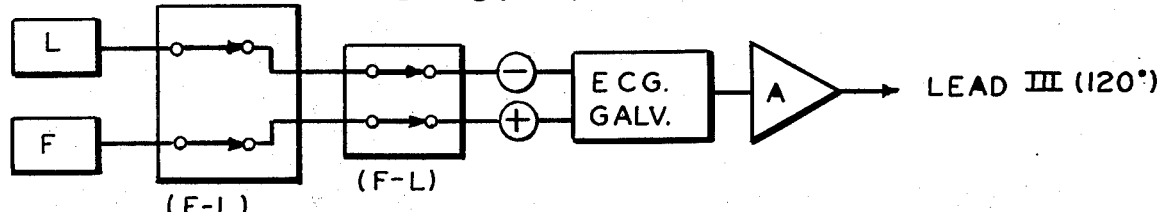
Figure 7:
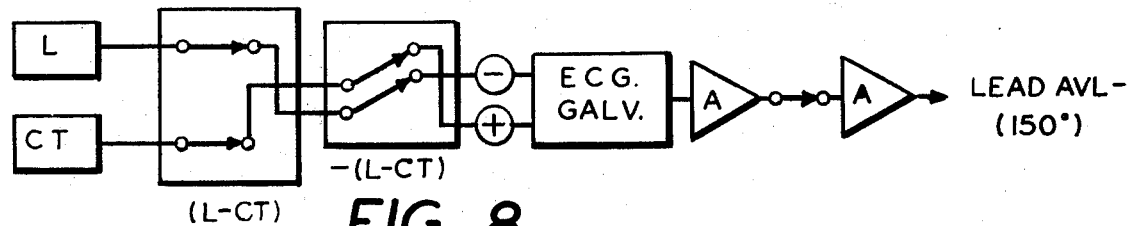
Figure 8:
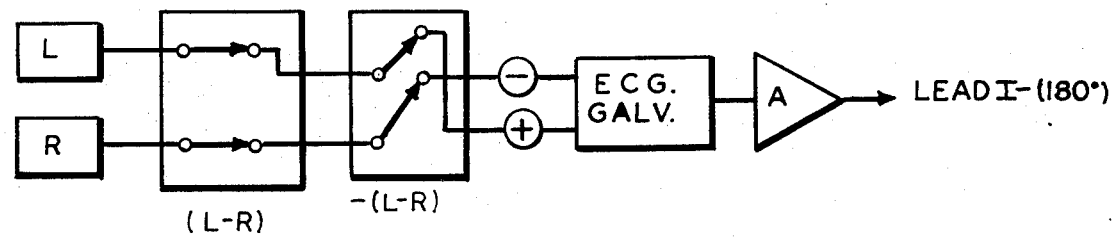
Figure 9:
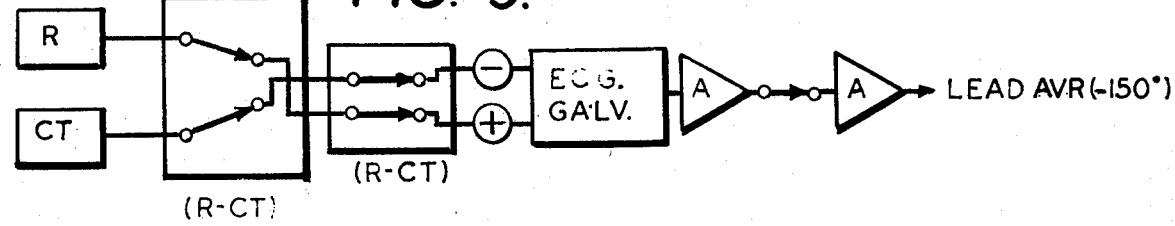
Figure 10:
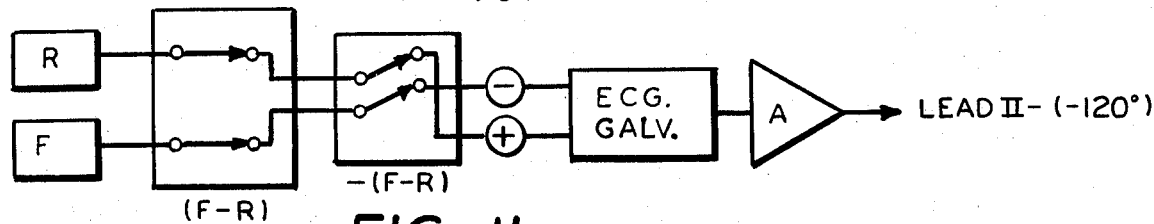
Figure 11:
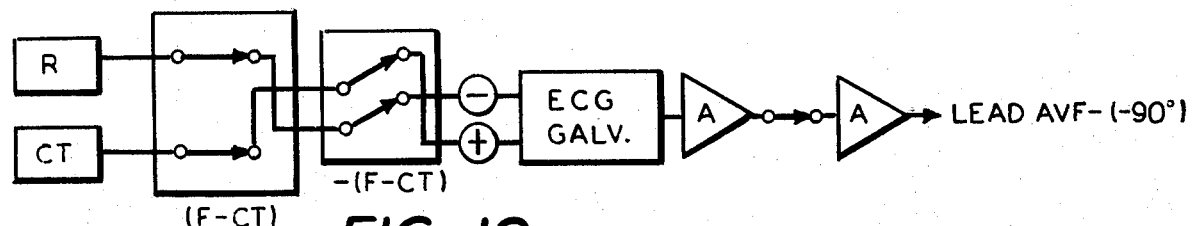
Figure 12:
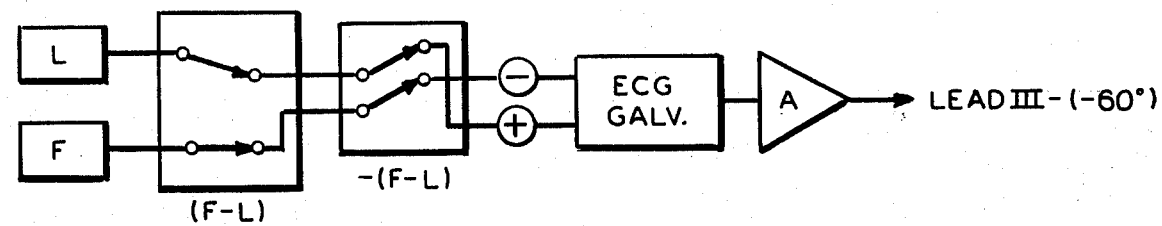
Figure 13:
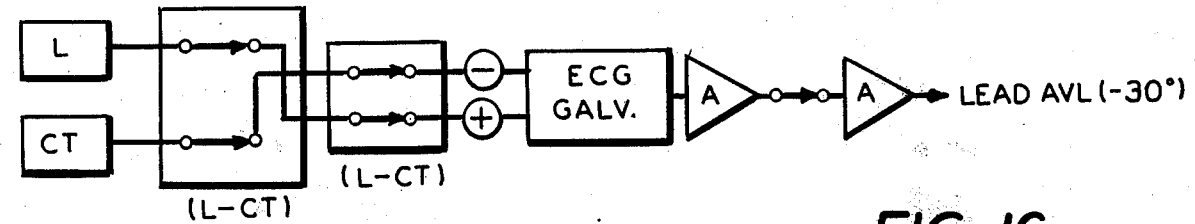

Referring now to FIGS. 2 through 13, the various settings for the electrode switch 46 and the polarity reversal switch 48, as well as switch 54, where appropriate, for the augmented V leads, is illustrated. For purposes of explanation, the electrode locations represented by the letters L, R and F are conventional for the Einthoven and augmented V leads, where L represents the left arm location, R represents the right arm location, and F represents the left leg location. As was previously mentioned, CT preferably represents the common terminal electrode according to Goldberger for providing the augmented V leads as illustrated by the configurations of FIGS. 14 through 16. FIG. 2 represents the various switch settings for providing the lead I input to the recorder 32, FIG. 3 represents the various switch settings for providing the lead AVR− input to the recorder 32, FIG. 4 represents the various switch settings for providing the lead II input to the recorder 32, FIG. 5 represents the various switch settings for providing the lead AVF input to the recorder 32, FIG. 6 represents the various switch settings for providing the lead III input to the recorder 32, FIG. 7 represents the various switch inputs for providing the lead AVL− input to the recorder 32, FIG. 8 represents the various switch settings for providing the lead I− input to the recorder 32, FIG. 9 represents the various switch settings for providing the lead AVR input to the recorder 32, FIG. 10 represents the various switch settings for providing the lead II− input to the recorder 32, FIG. 11 represents the various switch settings for providing the lead AVF− input to the recorder 32, FIG. 12 represents the various switch settings for providing the lead III− input to the recorder 32, and FIG. 13 represents the various switch settings for providing the lead AVL input to the recorder 32. The appropriate potential difference expression for the potential associated with the electrode pairs of FIGS. 2 through 13 is illustrated by the switches 46 and 48 with a minus symbol being placed outside the parentheses indicating the expression for the output of switch 48, as in FIGS. 3, 7, 8, 10, 11 and 12 to indicate that polarity reversal or inversion has occurred due to the setting of polarity reversal switch 48. Where no such polarity reversal occurs, due to the setting of polarity reversal switch 48, as indicated in FIGS. 2, 4, 5, 6, 9, and 13, the expression for the output of the polarity reversal switch 48 is identical to that representing the output of electrode selector switch 46. Thus, the expression for the potential difference associated with the lead I input is represented by the expression L—R, the potential difference associated with the lead AVR— input is represented by the expression —(R—CT) which is the inversion or polarity reversal of the lead AVR input potential illustrated in FIG. 9, the potential difference associated with the lead II input is represented by the expression F—R, the potential difference associated with the lead AVF input is represented by the expression F—CT, the potential difference associated with the lead III input is represented by the expression F—L, the potential difference associated with the lead AVL— input is represented by the expression —(L—CT) which is the inversion of polarity reversal of the lead AVL input potential illustrated in FIG. 13, the potential difference associated with the lead I— input is represented by the expression —(L—R) which is the polarity reversal of the lead I input potential illustrated in FIG. 2, the potential difference associated with the lead AVR input is represented by the expression R—CT, the potential difference associated with the lead II— input is represented by the expression —(F—R) which is the inversion or polarity reversal of the lead II input potential illustrated in FIG. 4, the potential difference associated with the lead AVF— input is represented by the expression —(F—CT) which is the inversion of polarity reversal of the lead AVF input potential illustrated in FIG. 5, the potential difference associated with the lead III— input is represented by the expression —(F—L) which is the inversion or polarity reversal of the lead III input potential represented by FIG. 6, and the potential difference associated with the lead AVL input is represented by the expression L—CT. Thus, as shown and preferred in FIGS. 1 through 18, the selector switch 46 and the polarity reversal switch 48 are controllably connected together in order to directly provide a 360° hexaxial reference system orthogonal display having 30° angular separation between adjacent electrode pair potential difference electrocardiogram sampled voltages for directly providing such an electrocardiogram, such as illustrated in FIG. 17, which may be more readily interpreted than conventional electrocardiograms, while providing additional information due to the inverted signals for the precardial leads which will simplify the diagnosis of certain types of infarctions such as posterior myocardial infarction.

What is claimed is:

1. In an electrocardiographic diagnostic apparatus having a plurality of electrodes disposable at predetermined locations with respect to the arms and legs of the body of a patient whose heart activity is to be diagnosed to provide both Einthoven bipolar leads and augmented V unipolar leads, each of said leads comprising an electrode pair, said diagnostic apparatus including display means for providing an orthogonal electrocardiogram display of voltage versus time generated at said predetermined locations in response to said heart activity, said bipolar electrode pairs being disposed so as to provide time sampled voltages comprising a first voltage potential difference having an associated polarity between the left arm and right arm electrode pair for said patient represented by the expression L—R, a second voltage potential difference having an associated polarity between the left leg and said right arm electrode pair for said patient represented by the expression F—R, and a third voltage potential difference having an associated polarity between said left leg and said left arm electrode pair for said patient represented by the expression F—L, where L represents the potential at said left arm electrode location, R represents the potential at said right arm electrode location and F represents the potential at said left leg electrode location, and said unipolar electrode pair being disposed with respect to a central electrode terminal so as to provide a fourth voltage potential difference having an associated polarity between said left arm electrode and said central electrode terminal represented by the expression L—CT, a fifth voltage potential difference having an associated polarity between said right arm electrode and said central electrode terminal represented by the expression R—CT, and a sixth voltage potential difference having an associated polarity between said left leg electrode and said central electrode terminal represented by the expression F—CT, where CT represents the potential at said central electrode terminal, the improvement comprising means connectable to said electrodes for receiving output signals therefrom for sequentially selecting one of said electrode pairs from said plurality of bipolar and unipolar electrode pairs for sequentially providing said display and selectable polarity reversal means connected between said electrode pair selection means and said display means for selectively reversing said associated polarity of said first, second, third, fourth, fifth and sixth voltage potential differences, said electrode pair selection means and said selectable polarity reversal means being controllably connected together for directly providing a 360° hexaxial reference system orthogonal display having 30° angular separation between adjacent electrode pair potential difference electrocardiographic sampled voltages as said orthogonal electrocardiogram display on said display means, said display comprising a contiguous sequential display of said first voltage angularly situated at 0° in said reference system, said fifth voltage with said associated polarity reversed angularly situated at 30° in said reference system, said second voltage angularly situated at 60° in said reference system, said sixth voltage angularly situated at 90° in said reference system, said third voltage angularly situated at 120° in said reference system, said fourth voltage with said associated polarity reversed angularly situated at 150° in said reference system, said first voltage with said associated polarity reversed angularly situated at 180° in said reference system, said fifth voltage angularly situated at —150° in said reference system, said second voltage with said associated polarity reversed angularly situated at —120° in said reference system, said sixth voltage with said polarity reversed angularly situated at —90° in said reference system, said third voltage with said polarity reversed angularly situated at —60° in said reference system, and said fourth voltage angularly situated at —30° in said reference system, whereby cardiogram analysis including determination of the mean vector is enhanced.

2. An improved electrocardiographic diagnostic apparatus in accordance with claim 1 further comprising amplifier means operatively connected between said polarity reversal means and said display means for amplifying said voltages provided thereto.

3. An improved electrocardiographic diagnostic apparatus in accordance with claim 2 wherein said amplifier means comprises means operatively connected to said sequential selection means for amplifying said fourth, fifth and sixth voltages with and without said associated polarity reversed which are associated with said unipolar electrode pairs a sufficient amount to insure substantially exact correspondence in said hexaxial reference system between voltages on any given vector therein between the Einthoven leads and the augmented V leads.

4. An improved electrocardiographic apparatus in accordance with claim 3 wherein said unipolar associated voltage amplification means comprises means for amplifying said unipolar associated voltages substantially by 13% to provide said correspondence.

5. An improved electrocardiographic diagnostic apparatus in accordance with claim 1 wherein said display means comprises an electrocardiogram recorder.

6. A method for directly providing a 360° hexaxial reference system orthogonal display of voltage versus time generated in response to heart activity, said display having 30° angular separation between adjacent electrode pair potential difference electrocardiographic time sampled voltages, said method comprising the steps of disposing a plurality of electrodes at predetermined locations with respect to the arms and legs of the body of a patient whose heart activity is to be diagnosed to provide both Einthoven bipolar leads and augmented V unipolar leads with each of said leads comprising an electrode pair for sensing the potential difference at said predetermined locations in response to said heart activity, said bipolar electrode pairs being disposed so as to provide time sampled voltages comprising a first voltage potential difference having an associated polarity between the left arm and right arm electrode pair for said patient represented by the expression L—R, a second voltage potential difference having an associated polarity between the left leg and said right arm electrode pair for said patient represented by the expression F—R, and a third voltage potential difference having an associated polarity between said left leg and said left arm electrode pair for said patient represented by the expression F—L, where L represents the potential at said left arm electrode location, R represents the potential at said right arm electrode location and F represents the potential at said left leg electrode location, and said unipolar electrode pairs being disposed with respect to a central electrode terminal so as to provide a fourth voltage potential difference having an associated polarity between said left arm electrode and said central electrode terminal represented by the expression L—CT, a fifth voltage potential difference having an associated polarity between said right arm electrode and said central electrode terminal represented by the expression R—CT, and a sixth voltage potential difference having an associated polarity between said left leg electrode and said central electrode terminal represented by the expression F—CT, where CT represents the potential at said central electrode terminal; sequentially selecting said electrode pairs one-by-one from said plurality of bipolar and unipolar electrode pairs for sequentially providing said display and selectively reversing said associated polarity of said first, second, third, fourth, fifth and sixth voltage potential differences, for directly providing said 360° hexaxial reference system orthogonal display as a contiguous sequential display of said first voltage angularly situated at 0° in said reference system, said fifth voltage with said associated polarity reversed angularly situated at 30° in said reference system, said second voltage angularly situated at 60° in said reference system, said sixth voltage angularly situated at 90° in said reference system, said third voltage angularly situated at 120° in said reference system, said fourth voltage with said associated polarity reversed angularly situated at 150° in said reference system, said first voltage with said associated polarity reversed angularly situated at 180° in said reference system, said fifth voltage angularly situated at —150° in said reference system, said second voltage with said associated polarity reversed angularly situated at —120° in said reference system, said sixth voltage with said polarity reversed angularly situated at —90° in said reference system, said third voltage with said polarity reversed angularly situated at —60° in said reference system, and said fourth voltage angularly situated at —30° in said reference system, whereby cardiogram analysis including determination of the mean vector is enhanced.

7. A method in accordance with claim 6 further comprising the step of amplifying said fourth, fifth and sixth voltages with and without said associated polarity reversed which are associated with said unipolar electrode pairs a sufficient amount to insure substantially exact correspondence in said hexaxial reference system between voltages on any given vector therein between the Einthoven leads and the augmented V leads.

8. A method in accordance with claim 7 wherein said amplifying step further comprises the step of amplifying said unipolar associated voltages substantially by 13% to provide said correspondence.

9. A method in accordance with claim 6 further comprising the step of providing said display as an electrocardiogram recording.

* * * * *